US009970900B2

(12) United States Patent
Kreppenhofer et al.

(10) Patent No.: US 9,970,900 B2
(45) Date of Patent: May 15, 2018

(54) METHODS FOR DISTINGUISHING DIOLEINATES OF AGED AND NON-AGED OLIVE OIL

(71) Applicant: DH Technologies Development Pte. Ltd., Singapore (SG)

(72) Inventors: Stefanie Kreppenhofer, Darmstadt (DE); Axel Besa, Bad Sassendorf (DE)

(73) Assignee: DH Technologies Development Pte. Ltd., Singapore (SG)

( * ) Notice: Subject to any disclaimer, the term of this patent is extended or adjusted under 35 U.S.C. 154(b) by 0 days. days.

(21) Appl. No.: 15/501,304

(22) PCT Filed: Jul. 24, 2015

(86) PCT No.: PCT/IB2015/055623
§ 371 (c)(1),
(2) Date: Feb. 2, 2017

(87) PCT Pub. No.: WO2016/020788
PCT Pub. Date: Feb. 11, 2016

(65) Prior Publication Data
US 2017/0219526 A1 Aug. 3, 2017

Related U.S. Application Data

(60) Provisional application No. 62/033,378, filed on Aug. 5, 2014.

(51) Int. Cl.
*H01J 49/00* (2006.01)
*G01N 27/62* (2006.01)
*G01N 33/03* (2006.01)

(52) U.S. Cl.
CPC ........... *G01N 27/624* (2013.01); *G01N 33/03* (2013.01); *H01J 49/0031* (2013.01); *H01J 49/0045* (2013.01)

(58) Field of Classification Search
None
See application file for complete search history.

(56) References Cited

U.S. PATENT DOCUMENTS

| 7,138,626 | B1* | 11/2006 | Karpetsky | G01N 27/624 250/288 |
| 7,429,731 | B1* | 9/2008 | Karpetsky | G01N 27/624 250/281 |

(Continued)

OTHER PUBLICATIONS

International Search Report and Written Opinion for PCT/IB2015/055623, dated Nov. 11, 2015.
(Continued)

*Primary Examiner* — Andrew Smyth
(74) *Attorney, Agent, or Firm* — John R. Kasha; Kelly L. Kasha; Kasha Law LLC

(57) ABSTRACT

Systems and methods are provided for selectively filtering 1,2-diolein and 1,3-dioleine ions from an olive oil sample. An ion source is instructed to ionize a mixture of an olive oil sample and a pre-ionization modifier. The pre-ionization modifier includes silver (Ag). A differential mobility spectrometry (DMS) device is instructed to separate ions received from the ion source and affected by a post-ionization modifier based on ion mobility. The second post-ionization modifier is butanol, for example. The DMS device is instructed to selectively filter separated 1,2-diolein precursor ions by selecting a first compensation voltage (CoV) for the DMS device. The first CoV is specific to separate 1,2-diolein precursor ions from 1,3-diolein precursor ions. The DMS device is instructed to selectively filter separated 1,3-diolein precursor ions by selecting a second CoV for the DMS device. The second CoV is specific to separate 1,3-diolein precursor ions from 1,2-diolein precursor ions.

15 Claims, 11 Drawing Sheets

(56) References Cited

U.S. PATENT DOCUMENTS

| | | | |
|---|---|---|---|
| 7,586,092 B1* | 9/2009 | Karpetsky | G01N 27/624 250/281 |
| 7,812,305 B2* | 10/2010 | Miller | G01N 27/624 250/281 |
| 8,384,024 B2* | 2/2013 | Miller | G01N 27/624 250/281 |
| 8,581,178 B2* | 11/2013 | Miller | G01N 27/624 250/282 |
| 9,305,762 B2* | 4/2016 | Covey | G01N 27/624 |
| 2004/0036018 A1 | 2/2004 | Deguchi et al. | |
| 2005/0133716 A1* | 6/2005 | Miller | G01N 27/624 250/293 |
| 2006/0249671 A1* | 11/2006 | Karpetsky | G01N 27/624 250/288 |
| 2006/0289745 A1* | 12/2006 | Miller | G01N 27/624 250/294 |
| 2008/0149824 A1* | 6/2008 | Miller | G01N 27/624 250/287 |
| 2010/0001182 A1* | 1/2010 | Burchfield | G01N 27/624 250/283 |
| 2010/0127163 A1 | 5/2010 | Zhdaneev et al. | |
| 2011/0133076 A1* | 6/2011 | Miller | G01N 27/624 250/287 |
| 2011/0183431 A1* | 7/2011 | Covey | G01N 27/624 436/173 |
| 2013/0092834 A1* | 4/2013 | Covey | G01N 27/624 250/288 |
| 2013/0284914 A1 | 10/2013 | Zaleski et al. | |

OTHER PUBLICATIONS

Anne-Laurence Dupont et al., 'Capillary electrophoresis with electrospray ionisation-mass spectrometry for the characterisation of degradation products in aged papers', Talanta, 2012, vol. 89, pp. 301-309.

J.J.B. Nevado et al., 'New CE-ESI-MS analytical method for the separation, identification and quantification of seven phenolic acids including three isomer compounds in virgin olive oil', Talanta, 2009, vol. 79, pp. 1238-1246.

* cited by examiner

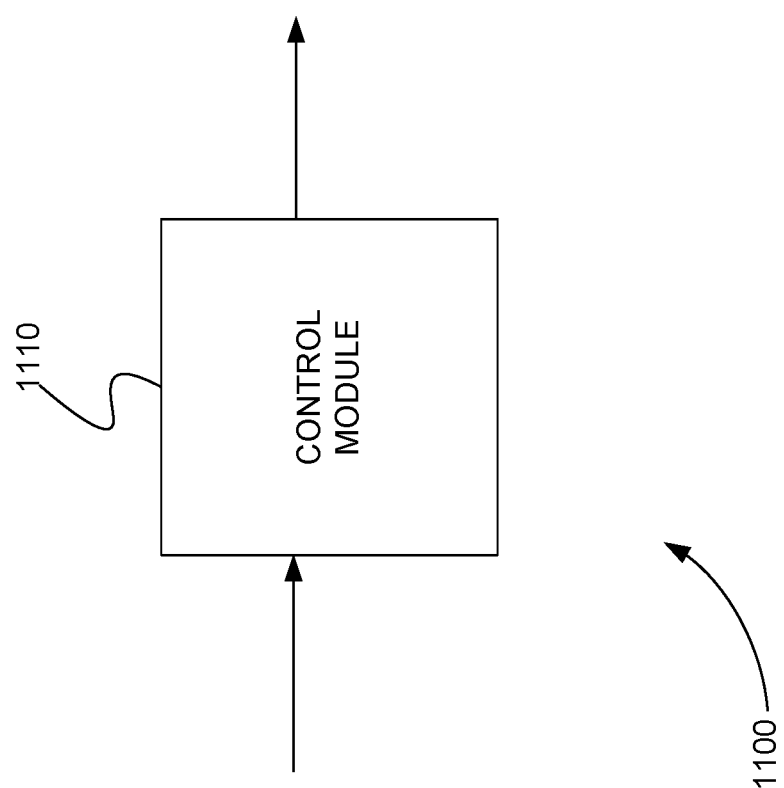

METHODS FOR DISTINGUISHING DIOLEINATES OF AGED AND NON-AGED OLIVE OIL

CROSS REFERENCE TO RELATED APPLICATION

This application claims the benefit of U.S. Provisional Patent Application Ser. No. 62/033,378, filed Aug. 5, 2014, the content of which is incorporated by reference herein in its entirety.

INTRODUCTION

The age of food and foodstuffs, particularly high cost foodstuffs, is an important piece of information for every consumer. As a result, foodstuff suppliers generally label many of their products with age related information, such as "sell by" and "expiration" dates. However, for regulatory agencies, determining the accuracy of this age related information is a difficult problem.

Olive oil is a high cost foodstuff that ages over time. As olive oil ages, some of its lipids belonging to the class of diglycerides change form, providing a biomarker that can be used to verify the age of olive oil. More specifically, over time, the compound 1,2-diolein becomes less abundant and the compound 1,3-dioleine becomes more abundant in olive oil.

Currently, for example, one way to measure these two compounds is by carbon-13 nuclear magnetic resonance ($^{13}C$ NMR), hydrogen nuclear resonance ($^{1}H$ NMR) or phosphorus 31 nuclear magnetic resonance ($^{31}P$ NMR) after derivatization of the diolein mixture to phosphorylated analogues. However, all techniques suffer from sensitivity and/or complexity of spectrum or are laborious and can only detect from micromole to millimole concentration range. Simpler techniques, such as chromatography, are typically unable to separate these two compounds in an acceptable amount of time.

As a result, systems and methods are needed to accurately separate the biomarkers 1,2-diolein and 1,3-dioleine in an olive oil sample and determine their relative quantities in the sample in order to determine the age of the sample.

SUMMARY

A system is disclosed for selectively filtering 1,2-diolein and 1,3-dioleine ions from an olive oil sample. The system includes an ion source, a differential mobility spectrometry (DMS) device, and a processor in communication with the ion source and the DMS device.

The ion source is configured to receive a mixture of an olive oil sample and a pre-ionization modifier and ionize the mixture. The DMS device is configured to receive ions from the ion source, to receive a post-ionization modifier from a modifier source, to separate ions affected by the modifier based on ion mobility, and to selectively filter separated ions based on a compensation voltage (CoV).

The processor instructs the ion source to ionize the olive oil sample, and instructs the DMS device to separate ions received from the ion source and affected by the post-ionization modifier based on ion mobility. The processor further instructs the DMS device to selectively filter separated 1,2-diolein precursor ions by selecting a first CoV for the DMS device, and instructs the DMS device to selectively filter separated 1,3-diolein precursor ions by selecting a second CoV for the DMS device.

A method is disclosed for selectively filtering 1,2-diolein and 1,3-dioleine ions from an olive oil sample. An ion source is instructed to ionize a mixture of an olive oil sample and a pre-ionization modifier using a processor. A DMS device is instructed to separate ions received from the ion source and affected by a post-ionization modifier based on ion mobility using the processor. The DMS device is instructed to selectively filter separated 1,2-diolein precursor ions by selecting a first CoV for the DMS device using the processor. The DMS device is instructed to selectively filter separated 1,3-diolein precursor ions by selecting a second CoV for the DMS device using the processor.

A computer program product is disclosed that includes a non-transitory and tangible computer-readable storage medium whose contents include a program with instructions being executed on a processor so as to perform a method for selectively filtering 1,2-diolein and 1,3-dioleine ions from an olive oil sample. The method includes providing a system, wherein the system comprises one or more distinct software modules, and wherein the distinct software modules comprise a control module.

The control module instructs an ion source to ionize a mixture of an olive oil sample and a pre-ionization modifier. The control module instructs a DMS device to separate ions received from the ion source and affected by a post-ionization modifier based on ion mobility. The control module instructs the DMS device to selectively filter separated 1,2-diolein precursor ions by selecting a first CoV for the DMS device. The control module instructs the DMS device to selectively filter separated 1,3-diolein precursor ions by selecting a second CoV for the DMS device.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

FIG. 11 is a schematic diagram of a system that includes one or more distinct software modules that performs a method for selectively filtering 1,2-diolein and 1,3-dioleine ions from an olive oil sample, in accordance with various embodiments.

Figure 1:
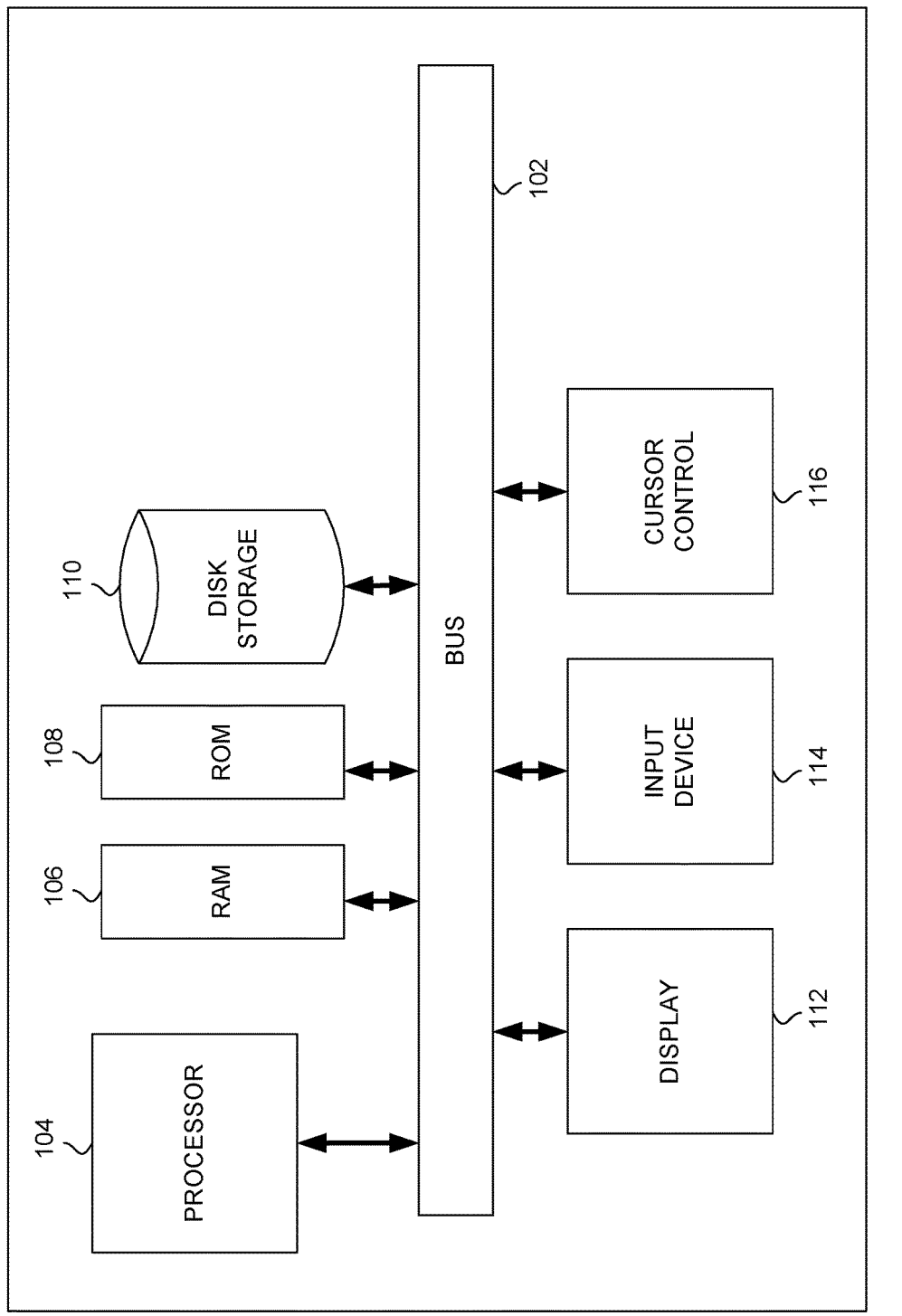
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods for Separation of Isobaric Dioleins

As described above, as olive oil ages, the compound 1,2-diolein becomes less abundant and the compound 1,3-dioleine becomes more abundant in olive oil, providing two biomarkers for assessing the age of olive oil. Unfortunately, current methods of measuring these compounds, such as phosphorus-31 nuclear magnetic resonance ($^{31}P$ NMR) spectroscopy and chromatography alone, are not accurate enough, suffer from sensitivity or take too much time to be useful for most regulatory agencies.

In various embodiments, differential mobility spectrometry (DMS) coupled with a multiple reaction monitoring (MRM) on tandem mass spectrometry method is used to quickly and accurately separate and differentiate the compounds 1,2-diolein and 1,3-dioleine in an olive oil sample. Each of the two compounds is then quantitated, and the ratio of the quantities of the two compounds is used to determine the age of the olive oil sample.

Figure 2:
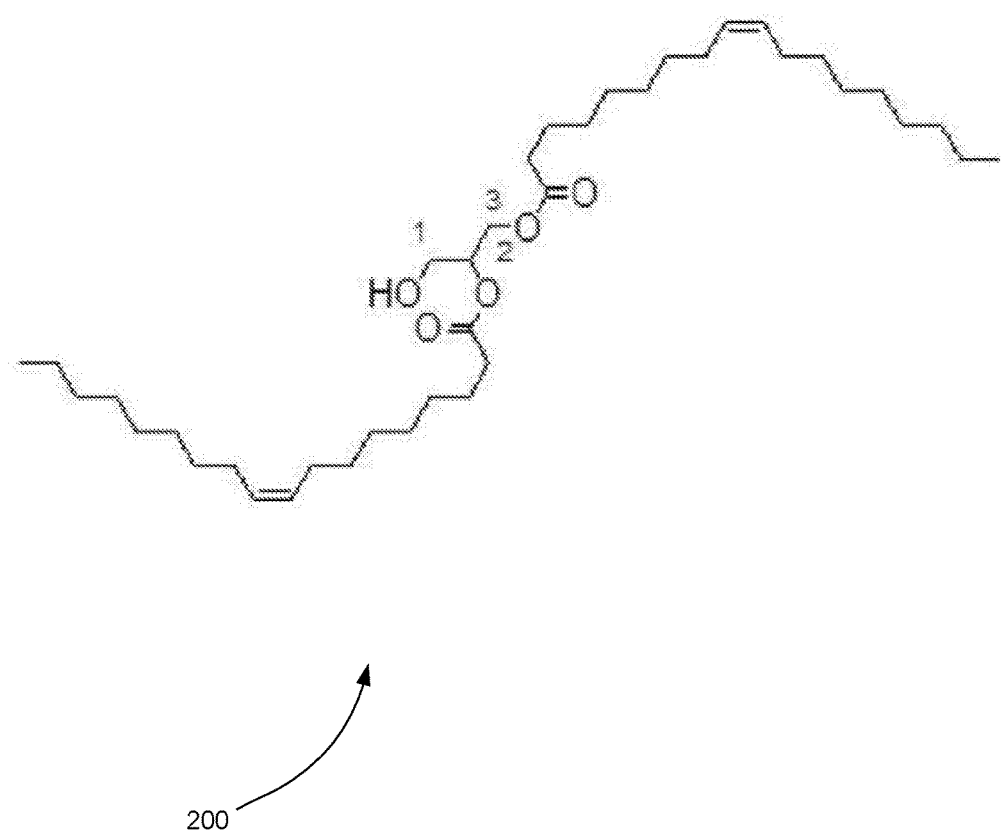
FIG. 2 is an exemplary diagram of the chemical structure of 1,2-diolein, in accordance with various embodiments.

FIG. 2 is an exemplary diagram of the chemical structure 200 of 1,2-diolein, in accordance with various embodiments.

Figure 3:
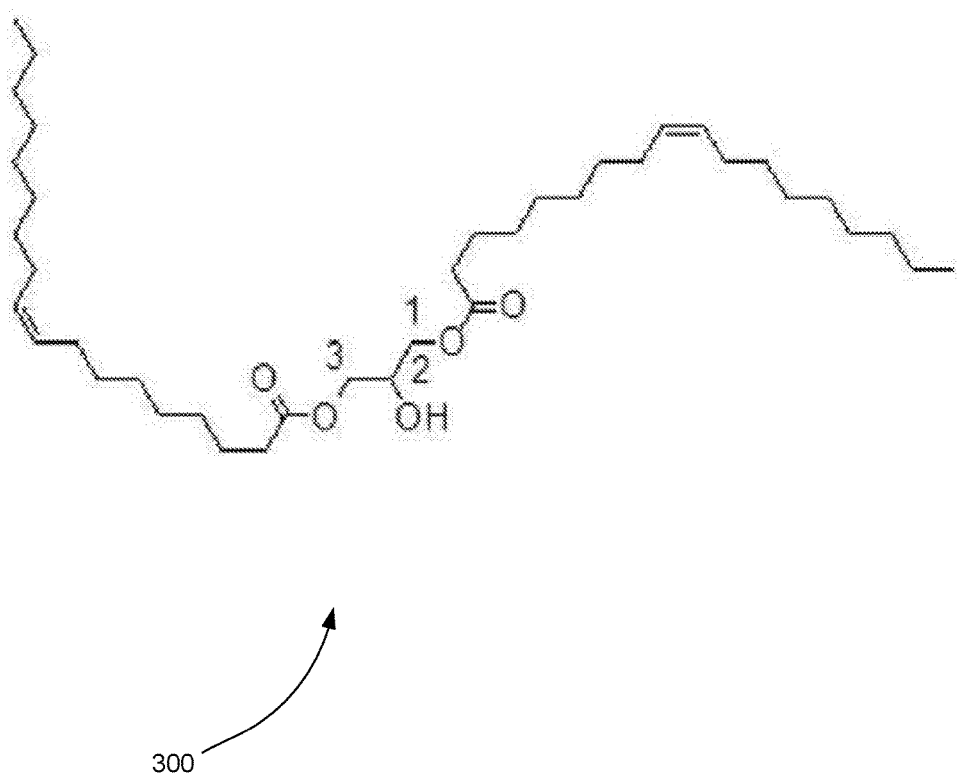
FIG. 3 is an exemplary diagram of the chemical structure of 1,3-diolein, in accordance with various embodiments.

FIG. 3 is an exemplary diagram of the chemical structure 300 of 1,3-diolein, in accordance with various embodiments.

FIGS. 2 and 3 show that 1,2-diolein and 1,3-diolein are isobaric and have exactly the same mass. The only structural differences between 1,2-diolein and 1,3-diolein are seen in their specific formation of the two oleic acids. Both 1,2-diolein and 1,3-diolein have the same dioleic acids.

As a result, when 1,2-diolein and 1,3-diolein are fragmented using tandem mass spectrometry, they produce the same two dioleic acid fragments or product ions. Consequently, it is not possible to separate 1,2-diolein and 1,3-diolein from an olive oil sample using tandem mass spectrometry alone. Similarly, it is difficult and laborious to use chromatography to separate 1,2-diolein and 1,3-diolein.

Figure 4:
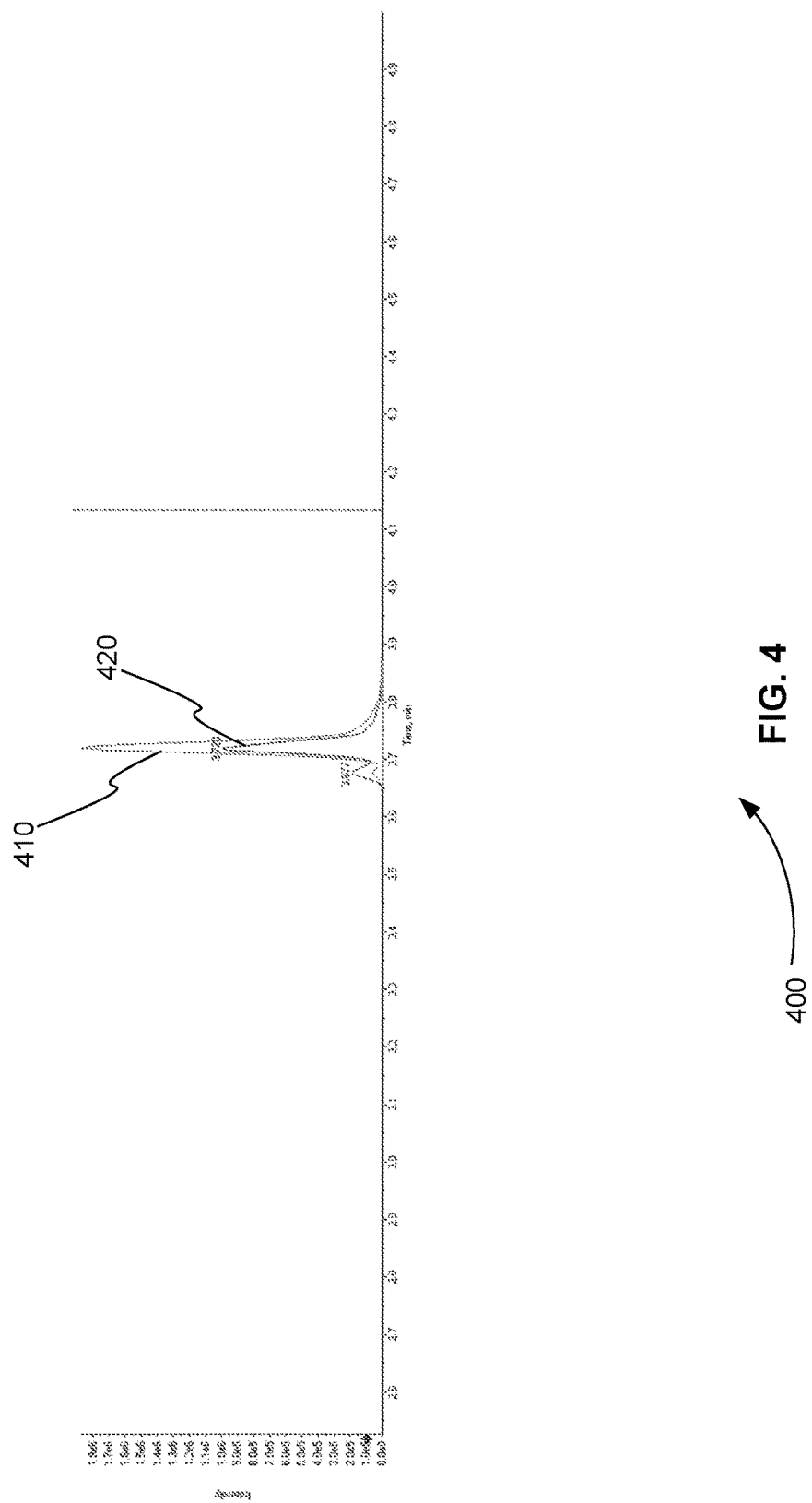
FIG. 4 is an exemplary plot showing the extracted ion current (XIC) for two product ions of 1,2-diolein from a multiple reaction monitoring (MRM) experiment performed on a sample containing only 1,2-diolein, in accordance with various embodiments.

FIG. 4 is an exemplary plot 400 showing the extracted ion current (XIC) for two product ions of 1,2-diolein from an MRM experiment performed on a sample containing only 1,2-diolein, in accordance with various embodiments. XIC 410, an ammonium adduct of 1,2-diolein, was measured using MRM transition with precursor mass of 638.5 Da to product ion with mass 339.2 Da, and XIC 420 was measured using MRM transition 638.5 Da to 603.6 Da. Plot 400 also shows that the product ion with mass 339.2 Da has a greater intensity than the product ion with mass 603.6 Da.

Figure 5:
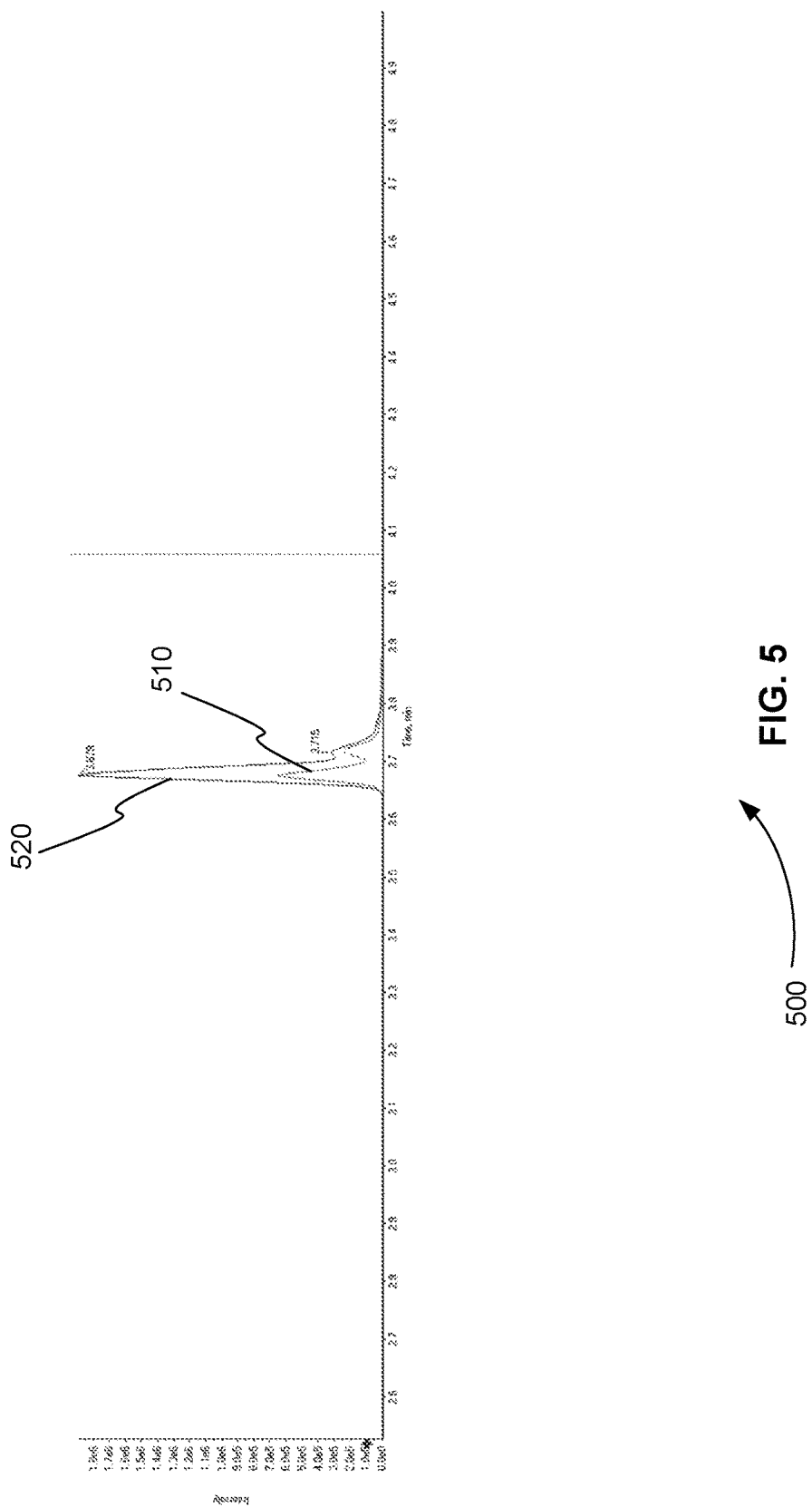
FIG. 5 is an exemplary plot showing the extracted ion current (XIC) for two product ions of 1,3-diolein from an MRM experiment performed on a sample containing only 1,3-diolein, in accordance with various embodiments.

FIG. 5 is an exemplary plot 500 showing the extracted ion current (XIC) for two product ions of 1,3-diolein from an MRM experiment performed on a sample containing only 1,3-diolein, in accordance with various embodiments. XIC 510 was measured for the product ion with mass 339.2 Da, and XIC 520 was measured for the product ion with mass 603.6 Da. 1,3-diolein has a precursor ion mass of 638.5 Da, for example. Plot 500 shows that 1,3-diolein elutes at about same retention time than 1,2-diolein. Plot 500 also shows that the product ion with mass 603.6 Da has a greater intensity than the product ion with mass 339.2 Da.

FIGS. 4 and 5 show that 1,2-diolein and 1,3-diolein have similar retention times making it difficult to use chromatography to separate the two compounds. Another factor affecting the chromatographic separation is the difference in the ratio of the product ions with different masses between the two compounds. In other words, the ratio of product ions with mass 339.2 Da versus product ions with mass 603.6 is different for 1,2-diolein and 1,3-diolein.

In various embodiments, a non-chromatographic separation technique is used to separate 1,2-diolein and 1,3-diolein from an olive oil sample. More specifically, differential mobility spectrometry (DMS) in combination with specific modifiers are used to separate 1,2-diolein and 1,3-diolein from an olive oil sample.

The separation of ions in a DMS device is based upon differences in their migration rates under high versus low electric fields. A high field is applied between the electrodes for a short period of time, and then a low field is applied in the opposite direction for a long period of time. Any difference between the low-field and high-field mobility of an ion of a compound of interest causes it to migrate towards one of the electrodes. The ion is steered back towards the center-line of the device by the application of a second voltage offset, known as the compensation voltage (CoV), a compound-specific parameter that can be used to selectively filter out all other ions. Rapid switching of the compensation voltage parameter allows the user to concurrently monitor many different compounds. An exemplary DMS device is the SelexION™ from AB SCIEX.

Modifiers are used with a DMS device to enhance the separation of a compound of interest. For example, a modifier builds an adduct with an ion of the compound of interest. Generally, the high field of the DMS device breaks the constituents of the adduct, while the low field of the DMS device reunites the constituents of the adduct. Essentially, the DMS device clusters and declusters the adduct. This clustering and declustering shows different effects, depending on specific nature of a given compound. Some clusters are more stable, and other clusters are less stable. The fact that some clusters are more stable than others produces different cross sections for compounds of interest. The different cross sections, in turn, produce separation, even at distances as short as three centimeters.

In various embodiments, 1,2-diolein and 1,3-diolein are separated from an olive oil sample using a DMS device, a modifier, and two different CoV values for the DMS device. In one preferred embodiment, 1,2-diolein and 1,3-diolein can be separated from an olive oil sample using a DMS device, silver acetate as pre-ionization modifier and butanol as a post-ionization modifier, and CoV values shows isomer specific values with base-line separation for the DMS device.

The silver ions of the modifier lead to adduct formation and may, for example, influence the cross sections of the 1,2-diolein and/or 1,3-diolein molecules. The fatty acids, sitting with dioleic acids of 1,2-diolein and 1,3-diolein have double bonds. If a modifier directly affects the double bonds, then the cross section of the molecule can be increased. Silver is positively charged, and may interact with the double bonds of 1,2-diolein and/or 1,3-diolein. Due to structural differences the molecular shape of at least one of the molecules, and in that way the cross section becomes more different from the other one.

Figure 6:
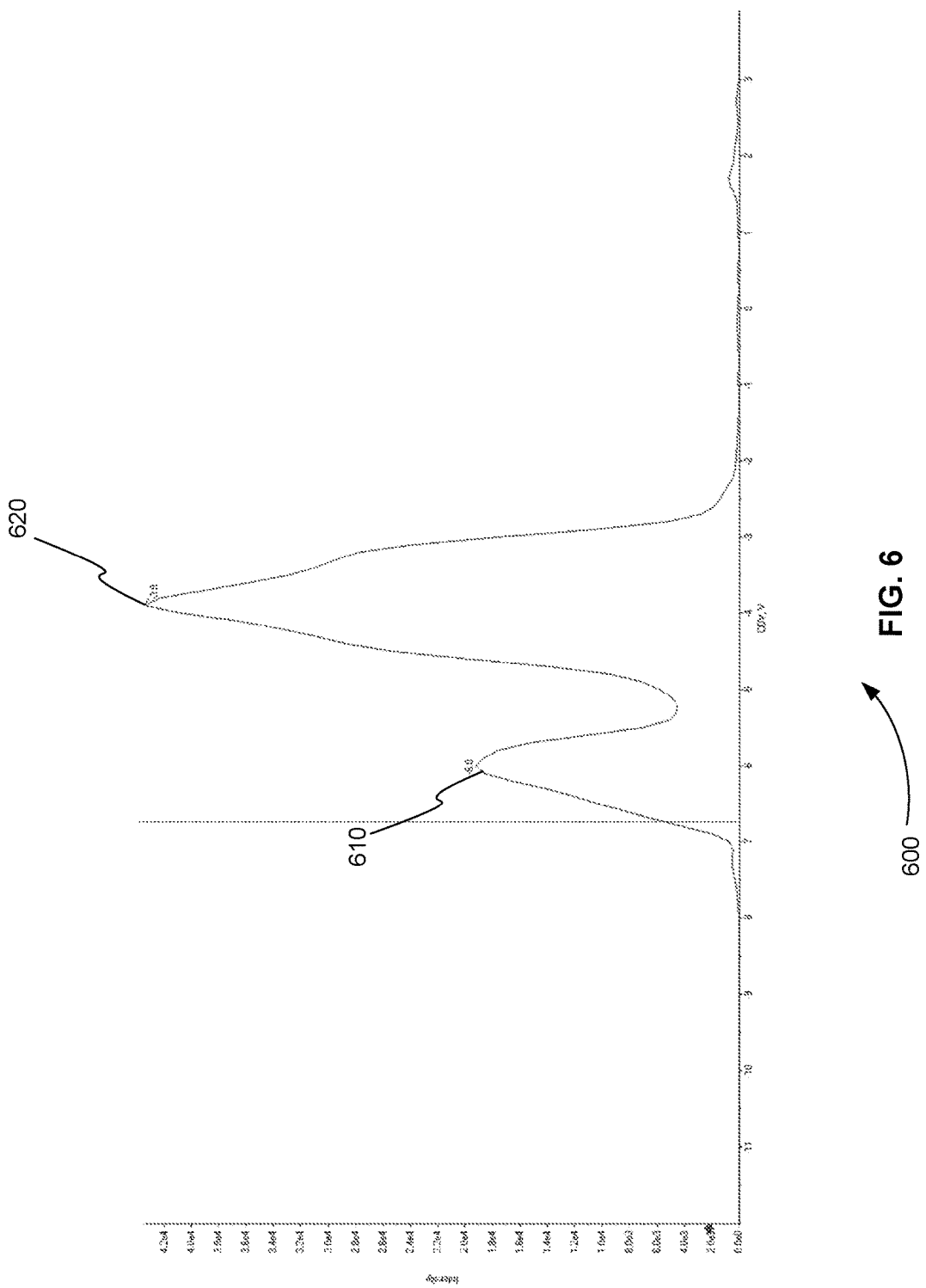
FIG. 6 is an exemplary plot of ion intensities of an MRM transition of silver adducts measured for a series of syringe pump experiments, where a 1:1 mixture of 1,2-diolein and 1,3-diolein was placed in a DMS device along with the modifiers butanol and silver acetate and the compensation voltage (CoV) was varied, in accordance with various embodiments.

FIG. 6 is an exemplary plot 600 of ion intensities of a multiple reaction monitoring (MRM) transition of silver adducts measured for a series of syringe pump experiments, where a 1:1 mixture of 1,2-diolein and 1,3-diolein containing silver acetate was placed in a DMS device along with the modifier butanol and the compensation voltage (CoV) was continuously varied, in accordance with various embodiments. Plot 600 shows ion intensity peaks 610 and 620. Through other experimentation, peak 610 was verified to correspond to the silver adduct of 1,2-diolein and peak 620 was verified to correspond to the silver adduct of 1,3-diolein. Using specific temperature, resolution settings and separation voltage Peak 610 has a maximum intensity at about −6.0 volts, and peak 620 has a maximum intensity at about −3.8 volts. As a result, it was found that 1,2-diolein can be separated at a CoV of about −6.0 volts, and 1,3-diolein can be separated at a CoV of about −3.8 volts. The MRM transition was precursor silver adduct mass 727.3 Da to oleic acid silver adduct fragment mass 389.1 Da.

Since 1,2-diolein and 1,3-diolein can be separated from an olive oil sample using a DMS device, a modifier, and two different CoV values, this separation technique can be incorporated into a standard MRM quantitation method and 1,2-diolein and 1,3-diolein can be quantitated without any additional separation technology. In other words, this separation technique can be incorporated into a standard MRM liquid chromatography/mass spectrometry/mass spectrometry (LC/MS/MS) method in order to sensitive quantitate the 1,2-diolein and 1,3-diolein product ions (=LC/DMS/MS/MS) or can be used as fast screening quantitation approach using infusion/differential mobility spectrometry (DMS)/mass spectrometry/mass spectrometry (infusionDMS/MS/MS). Because the CoV of the DMS device can be rapidly switched between two values, as described above, 1,2-diolein and 1,3-diolein product ions can be quantitated essentially in parallel. Once the quantities of the 1,2-diolein and 1,3-diolein product ions are determined, a ratio, for example, of these two values can be used to describe the age of the olive oil sample.

Figure 7:
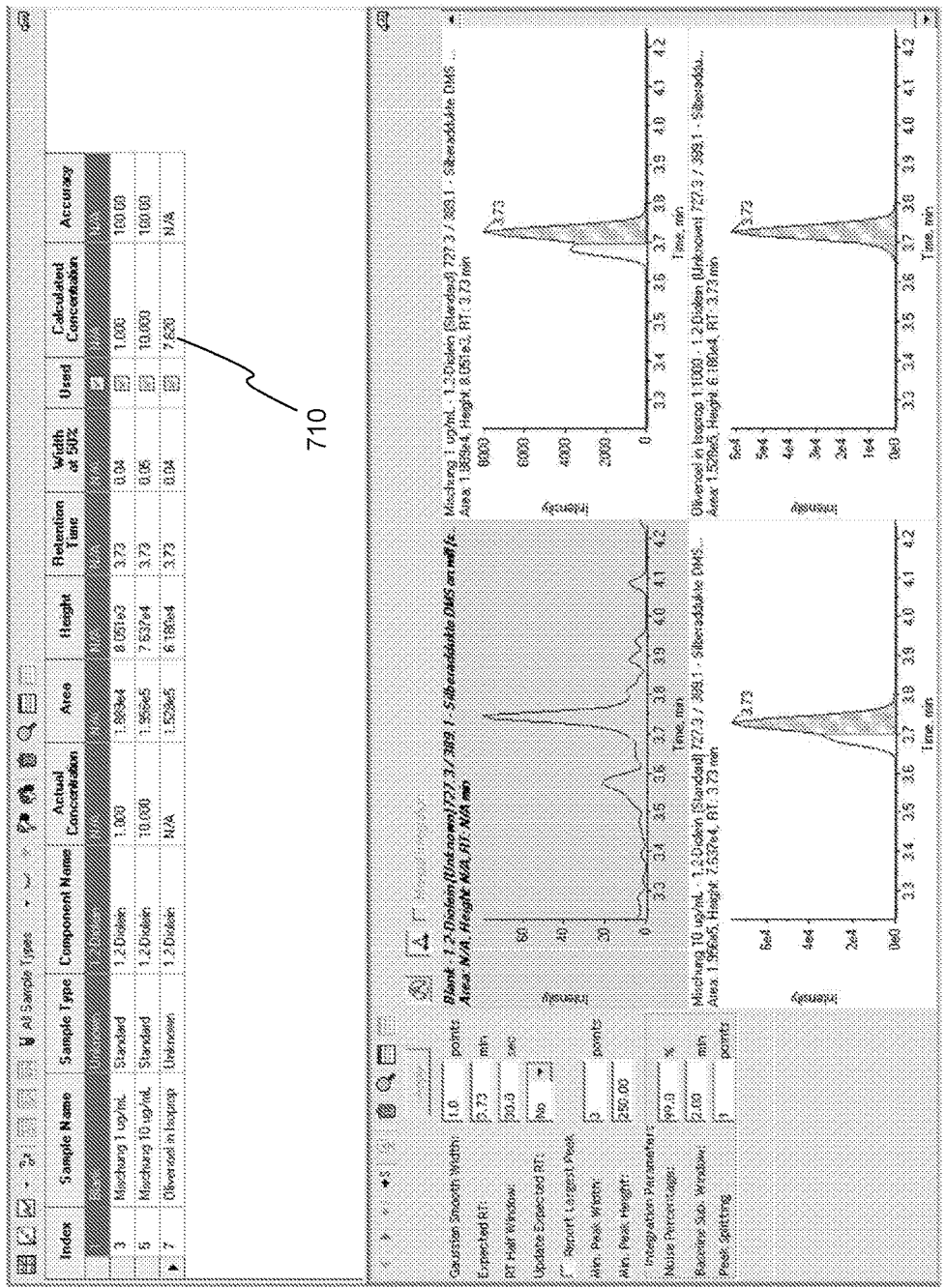
FIG. 7 is an exemplary screen capture from an MRM LC/MS/MS method, where 1,2-diolein and 1,3-diolein precursor ions are separated from an olive oil sample using a DMS device, a modifier, and two different CoV values, showing the quantitation of 1,2-diolein product ions in the olive oil sample, in accordance with various embodiments.

FIG. 7 is an exemplary screen capture 700 from an MRM LC/MS/MS method, where 1,2-diolein and 1,3-diolein precursor ions are separated from an olive oil sample using a DMS device, a pre-ionization and a post-ionization modifier, and two different CoV values, showing the quantitation of 1,2-diolein product ions in the olive oil sample, in accordance with various embodiments. FIG. 7 shows that concentration 710 is calculated for 1,2-diolein product ions. Concentration 710, a 1:1000 diluted, exemplary olive oil sample is 7.82 μg/mL.

Figure 8:
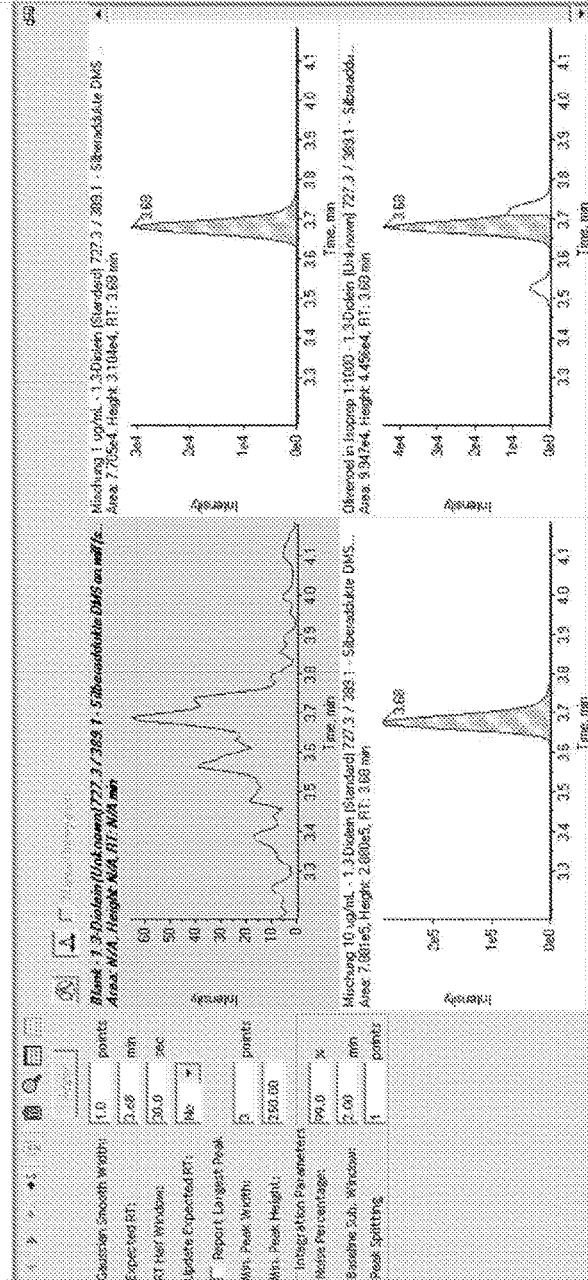
FIG. 8 is an exemplary screen capture from an MRM LC/MS/MS method, where 1,2-diolein and 1,3-diolein precursor ions are separated from an olive oil sample using a DMS device, a modifier, and two different CoV values, showing the quantitation of 1,3-diolein product ions in the olive oil sample, in accordance with various embodiments.

FIG. 8 is an exemplary screen capture 800 from an MRM LC/MS/MS method, where 1,2-diolein and 1,3-diolein precursor ions are separated from an olive oil sample using a DMS device, a modifier, and two different CoV values, showing the quantitation of 1,3-diolein product ions in the olive oil sample, in accordance with various embodiments. FIG. 8 shows that concentration 810, a 1:1000 diluted, exemplary olive oil sample is calculated for 1,3-diolein product ions. Concentration 810 is 1.28 μg/mL.

FIGS. 7 and 8 show that 1,2-diolein product ions have a much higher concentration in the olive oil sample than 1,3-diolein product ions. Since 1,2-diolein is more abundant in newer olive oil than 1,3-diolein, FIGS. 7 and 8 show that the olive oil sample is relatively new. The age of the olive oil is also a quality factor. Some olive oils are labeled a native or non-native. The methods described herein, therefore, can also be used to distinguish between native or non-native olive oils. In other words, these methods can also be used to determine if the olive is mislabeled or counterfeit.

The benefits of the methods and systems described herein include lower cost per sample, ease of use, and increased sensitivity. Customers get the results faster and cheaper.

Using ion mobility coupled with mass spectrometry high throughput sample analysis produces results faster and in a more cost effective way. Ion mobility with mass spectrometry can be provided in a bench-top instrument that is more efficient to move around if needed. AB SCIEX instruments, such as the TripleQuad or QTRAP, can be equipped with the SelexION™ DMS, for example.

System for Selectively Filtering Isobaric Dioleins

Figure 9:
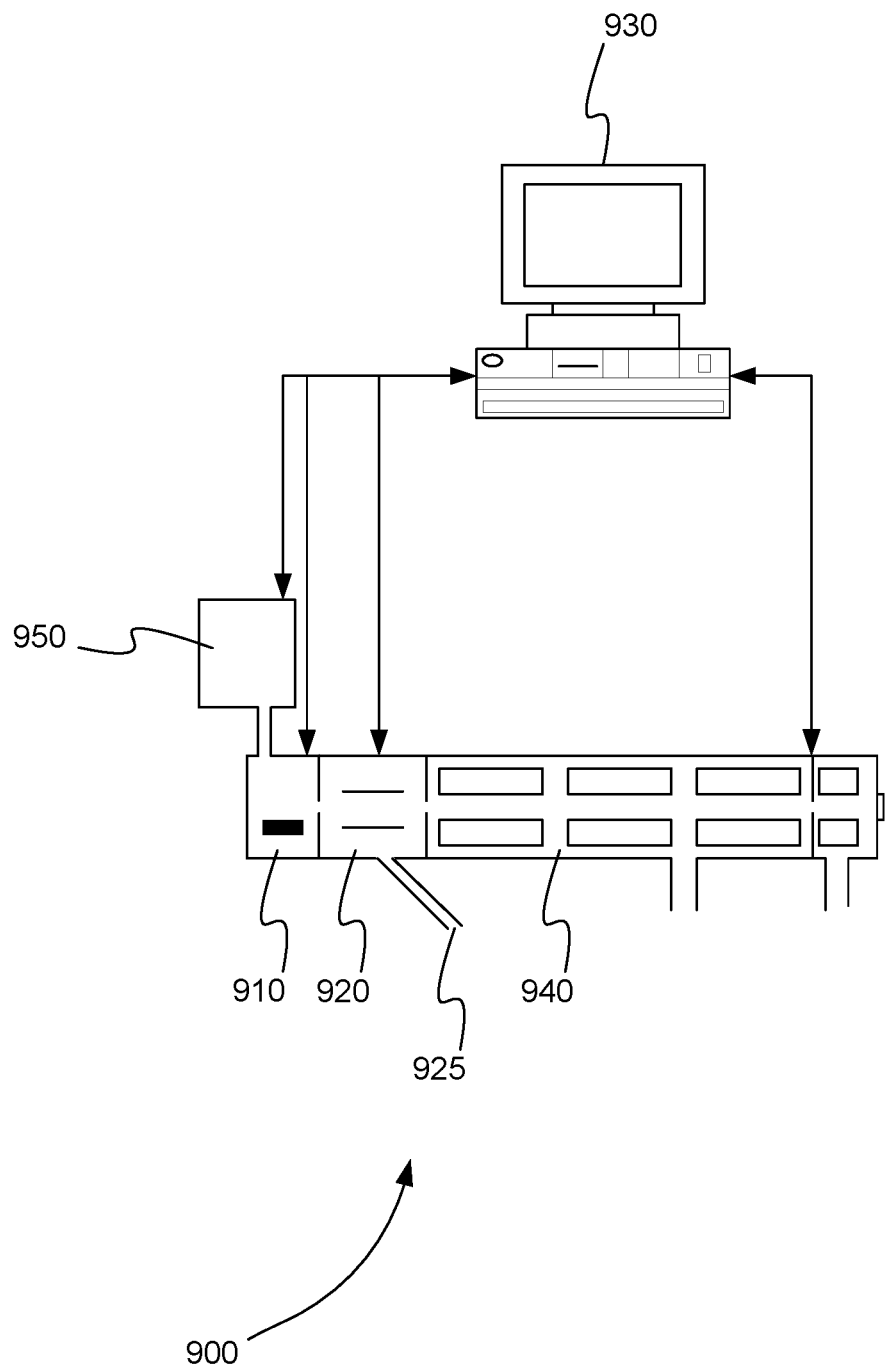
FIG. 9 is a schematic diagram of system for selectively filtering 1,2-diolein and 1,3-dioleine ions from an olive oil sample, in accordance with various embodiments.

FIG. 9 is a schematic diagram of system 900 for selectively filtering 1,2-diolein and 1,3-dioleine ions from an olive oil sample, in accordance with various embodiments. System 900 includes ion source 910, DMS device 920, and processor 930. Ion source 910 is configured to receive a mixture of an olive oil sample and a pre-ionization modifier and ionize the mixture received. In various embodiments, the pre-ionization modifier includes silver (Ag). The pre-ionization modifier is, for example, silver acetate.

DMS device 920 is configured to receive ions from ion source 910, to receive a post-ionization modifier from a modifier source 925, to separate ions affected by the post-ionization modifier based on ion mobility, and to selectively filter separated ions based on a compensation voltage. In various embodiments the post-ionization modifier is butanol. In various alternative embodiments, the post-ionization modifier can be any related homologue of butanol (e.g., pentanol, hexanol, heptanol, etc.)

Processor 930 can be, but is not limited to, a computer, microprocessor, microcontroller, the computer system of FIG. 1, or any device capable of controlling devices, processing data, and sending and receiving data. Processor 930 is in communication with ion source 910 and DMS device 920.

Processor 930 instructs ion source 930 to ionize the olive oil sample. Processor 930 instructs DMS device 920 to separate ions received from ion source 910 and affected by the post-ionization modifier based on ion mobility. Processor 930 instructs DMS device 920 to selectively filter separated 1,2-diolein precursor ions by selecting a first compensation voltage (CoV) for DMS device 920. Processor 930 instructs DMS device 920 to selectively filter separated 1,3-diolein precursor ions by selecting a second compensation voltage (CoV) for DMS device 920.

In various embodiments, the first CoV is different from or base line separated from second CoV. One of ordinary skill in the art can understand that these CoV values can vary due to e.g., chosen DMS temperature, resolution and/or separation voltage.

In various embodiment, the selectively filtered 1,2-diolein precursor ions can be adducts of 1,2-diolein ions and the pre-ionization modifier, and the selectively filtered 1,3-diolein precursor ions can be adducts of 1,3-diolein ions and the pre-ionization modifier. In other words, the selectively filtered 1,2-diolein and 1,3-diolein precursor ions can include silver, for example.

In various embodiments, system 900 can also include tandem mass spectrometer 940. Tandem mass spectrometer 940 can include one or more physical mass analyzers that perform two or more mass analyses. A mass analyzer of a tandem mass spectrometer 940 can include, but is not limited to, a time of flight (TOF), a quadrupole, an ion trap, a linear ion trap, an orbitrap, or a Fourier transform mass analyzer.

Tandem mass spectrometer 940 is in communication with processor 930. Tandem mass spectrometer 940 is configured to receive selected separated ions from DMS device 920 and perform tandem mass spectrometry. Processor 930 further instructs tandem mass spectrometer 940 to perform tandem mass spectrometry on an MRM transition of the separated and filtered 1,2-diolein precursor ions, producing a product ion spectrum for the separated and filtered 1,2-diolein precursor ions. Likewise, processor 930 further instructs tandem mass spectrometer 940 to perform tandem mass spectrometry on an MRM transition of the separated and filtered 1,3-diolein precursor ions, producing a product ion spectrum for the separated and filtered 1,3-diolein precursor ions.

In various embodiments, system 900 can be used to quantitate the 1,2-diolein and 1,3-diolein product ions. For example, an MRM separation coupled mass spectrometry/mass spectrometry (MS/MS) or tandem mass spectrometry method is performed to quantitate the 1,2-diolein and 1,3-diolein product ions using system 900. System 900 also includes, for example, separation device 950. Separation device 950 can perform a separation technique that includes, but is not limited to, liquid chromatography, gas chromatography, capillary electrophoresis, or ion mobility.

Separation device 950 is in communication with processor 930. Separation device 950 is configured to separate diglycerides from olive oil. Processor 930 instructs separation device 950 to separate diglycerides from olive oil over time producing the olive oil sample. Processor 930 instructs ion source 910 to ionize the mixture of the olive oil sample and the pre-ionization modifier each time step of a plurality of time steps. The pre-ionization modifier is, for example, infused by additional pump (not shown) after separation of diglycerides from the olive oil by separation device 950, but before ionization by ion source 910. Processor 930 is also in communication with the additional pump and instructs the pump to provide the infusion.

Processor 930 instructs DMS device 920 to separate ions received from ion source 910 and affected by the post-ionization modifier based on ion mobility at each time step. Processor 930 instructs DMS device 920 to selectively filter separated 1,2-diolein precursor ions by selecting a first compensation voltage (CoV) for DMS device 920 at each time step. Processor 930 also instructs DMS 920 to selectively filter separated 1,3-diolein precursor ions by selecting a second compensation voltage (CoV) for DMS device 920 at each time step.

Processor 930 instructs tandem mass spectrometer 940 to perform tandem mass spectrometry on an MRM transition of the separated and filtered 1,2-diolein precursor ions at each time step, producing a plurality product ion spectra for the separated and filtered 1,2-diolein precursor ions for the plurality of time steps. Processor 930 also instructs tandem mass spectrometer 940 to perform tandem mass spectrometry on an MRM transition of the separated and filtered 1,3-diolein precursor ions at each time step, producing a plurality product ion spectra for the separated and filtered 1,3-diolein precursor ions for the plurality of time steps.

Processor 930 further calculates an extracted ion current for 1,2-diolein product ions from the plurality product ion spectra for the separated and filtered 1,2-diolein precursor ions for the plurality of time steps. Processor 930 also calculates an extracted ion current for 1,3-diolein product ions from the plurality product ion spectra for the separated and filtered 1,3-diolein precursor ions for the plurality of time steps.

Processor 930 further quantitates 1,2-diolein product ions in the olive oil sample from the extracted ion current for 1,2-diolein product ions, and quantitates 1,3-diolein product ions in the olive oil sample from the extracted ion current for 1,3-diolein product ions.

In various embodiments, processor 930 further calculates a ratio of the quantities of the 1,2-diolein product ions and the 1,3-diolein product ions. Processor 930, for example, reports this ratio to a user as an indication of the age of the olive oil sample.

Method for Selectively Filtering Isobaric Dioleins

Figure 10:
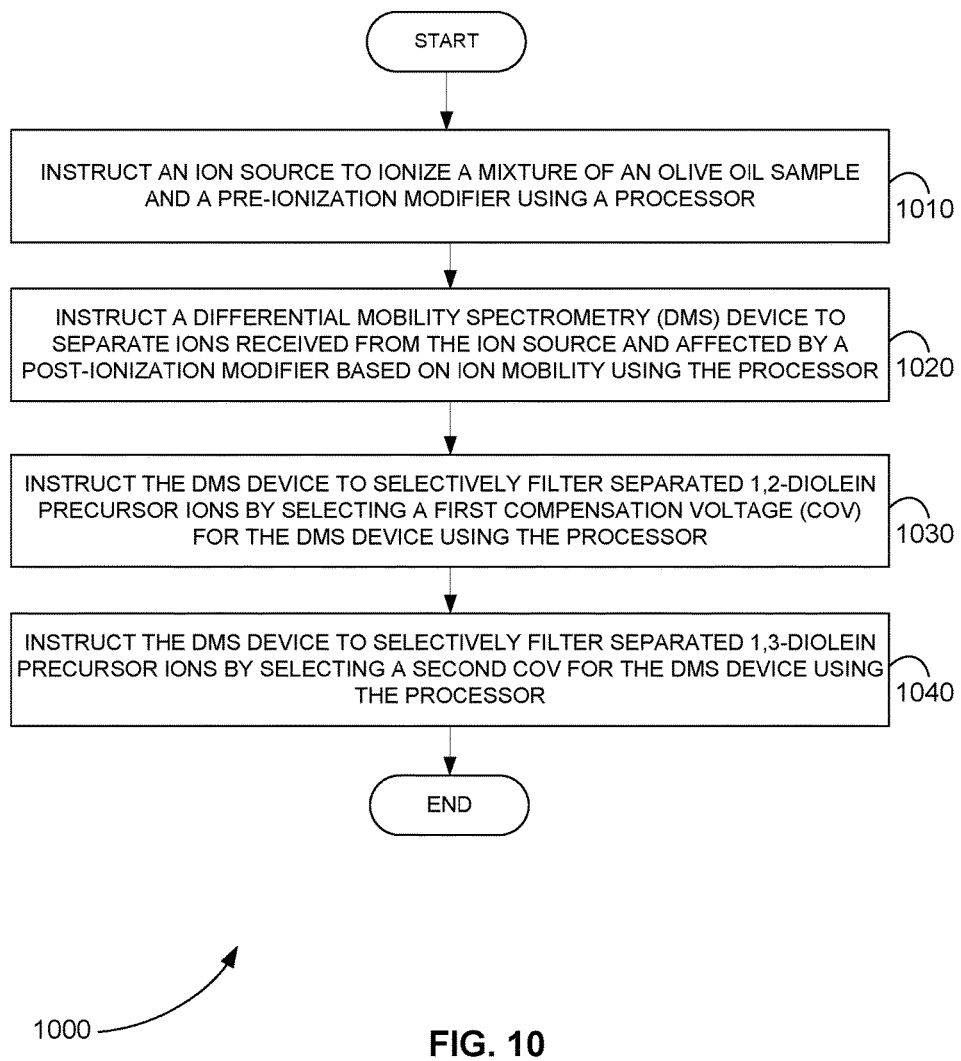
FIG. 10 is a flowchart showing a method for selectively filtering 1,2-diolein and 1,3-dioleine ions from an olive oil sample, in accordance with various embodiments.

FIG. 10 is a flowchart showing a method 1000 for selectively filtering 1,2-diolein and 1,3-dioleine ions from an olive oil sample, in accordance with various embodiments.

In step 1010 of method 1000, an ion source is instructed to ionize a mixture of an olive oil sample and a pre-ionization modifier using a processor. In various embodiments, the pre-ionization modifier includes silver.

In step 1020, a differential mobility separation (DMS) device is instructed to separate ions received from the ion source and affected by a post-ionization modifier based on ion mobility using the processor. In various embodiments, the post-ionization modifier includes butanol.

In step 1030, the DMS device is instructed to selectively filter separated 1,2-diolein precursor ions by selecting a first compensation voltage (CoV) for the DMS device using the processor.

In step 1040, the DMS device is instructed to selectively filter separated 1,3-diolein precursor ions by selecting a second CoV for the DMS device using the processor.

Computer Program Product for Selectively Filtering Isobaric Dioleins

In various embodiments, computer program products include a tangible computer-readable storage medium whose contents include a program with instructions being executed on a processor so as to perform a method for selectively filtering 1,2-diolein and 1,3-dioleine ions from an olive oil sample. This method is performed by a system that includes one or more distinct software modules.

FIG. 11 is a schematic diagram of a system 1100 that includes one or more distinct software modules that performs a method for selectively filtering 1,2-diolein and 1,3-dioleine ions from an olive oil sample, in accordance with various embodiments. System 1100 includes control module 1110.

Control module 1110 instructs an ion source to ionize a mixture of an olive oil sample and a pre-ionization modifier. Control module 1110 instructs differential mobility separation (DMS) device to separate ions received from the ion source and affected by a post-ionization modifier based on ion mobility using the control module. In various embodiments, the pre-ionization modifier includes silver, and post-ionization modifier includes is butanol.

Control module 1110 instructs the DMS device to selectively filter separated 1,2-diolein precursor ions by selecting a first compensation voltage (CoV) for the DMS device. Control module 1110 instructs the DMS device to selectively filter separated 1,3-diolein precursor ions by selecting a second CoV for the DMS device using the control module While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for selectively filtering 1,2-diolein and 1,3-dioleine ions from an olive oil sample, comprising:
   an ion source configured to receive a mixture of an olive oil sample and a pre-ionization modifier and ionize the mixture;
   a differential mobility spectrometry (DMS) device configured to receive ions from the ion source, to receive a post-ionization modifier from a modifier source, to separate ions affected by the modifier based on ion mobility, and to selectively filter separated ions based on a compensation voltage (CoV);
   a processor in communication with the ion source and the DMS device that
      instructs the ion source to ionize the olive oil sample,
      instructs the DMS device to separate ions received from the ion source and affected by the post-ionization modifier based on ion mobility,
      instructs the DMS device to selectively filter separated 1,2-diolein precursor ions by selecting a first CoV for the DMS device, and
      instructs the DMS device to selectively filter separated 1,3-diolein precursor ions by selecting a second CoV for the DMS device.

2. The system of claim 1, wherein the pre-ionization modifier comprises silver (Ag).

3. The system of claim 1, wherein the post-ionization modifier comprises butanol.

4. The system of claim 1, wherein the post-ionization modifier comprises a related higher homologue of butanol.

5. The system of claim 1, wherein the first CoV is different from the second CoV.

6. The system of claim 1, wherein the separated 1,2-diolein ions comprise adducts of 1,2-diolein ions and the modifier.

7. The system of claim 1, wherein the separated 1,3-diolein ions comprise adducts of 1,3-diolein ions and the modifier.

8. The system of claim 1, further comprising a tandem mass spectrometer in communication with the processor and configured to receive selected separated ions from the DMS device and perform tandem mass spectrometry, wherein the processor further
   instructs the tandem mass spectrometer to perform tandem mass spectrometry on a multiple reaction monitoring (MRM) transition of the separated and filtered 1,2-diolein precursor ions, producing a product ion spectrum for the separated and filtered 1,2-diolein precursor ions, and
   instructs the tandem mass spectrometer to perform tandem mass spectrometry on an MRM transition of the separated and filtered 1,3-diolein precursor ions, producing a product ion spectrum for the separated and filtered 1,3-diolein precursor ions.

9. The system of claim 8, further comprising a separation device in communication with the processor and configured to separate diglycerides from olive oil, wherein the processor
   instructs the separation device to separate diglycerides from olive oil over time, producing the olive oil sample,
   instructs the ion source to ionize the mixture of the olive oil sample and the pre-ionization modifier at each time step of a plurality of time steps,
   instructs the DMS device to separate ions received from the ion source and affected by the post-ionization modifier based on ion mobility at the each time step,
   instructs the DMS device to selectively filter separated 1,2-diolein precursor ions by selecting a first compensation voltage (CoV) for the DMS device at the each time step,
   instructs the DMS device to selectively filter separated 1,3-diolein precursor ions by selecting a second CoV for the DMS device at the each time step,
   instructs the tandem mass spectrometer to perform tandem mass spectrometry on a multiple reaction monitoring (MRM) transition of the separated and filtered 1,2-diolein precursor ions at the each time step, producing a plurality product ion spectra for the separated and filtered 1,2-diolein precursor ions for the plurality of time steps, and
   instructs the tandem mass spectrometer to perform tandem mass spectrometry on an MRM transition of the separated and filtered 1,3-diolein precursor ions at the each time step, producing a plurality product ion spectra for the separated and filtered 1,3-diolein precursor ions.

10. The system of claim 9, wherein the processor further calculates an extracted ion current for 1,2-diolein product ions from the plurality product ion spectra for the separated and filtered 1,2-diolein precursor ions for the plurality of time steps, and calculates an extracted ion current for 1,3-diolein product ions from the plurality product ion spectra for the separated and filtered 1,3-diolein precursor ions for the plurality of time steps.

11. The system of claim 10, wherein the processor further quantitates 1,2-diolein product ions in the olive oil from the extracted ion current for 1,2-diolein product ions and quantitates 1,3-diolein product ions in the olive oil from the extracted ion current for 1,3-diolein product ions.

12. The system of claim 11, wherein the processor further calculates a ratio of the quantities of the 1,2-diolein product ions and the 1,3-diolein product ions.

13. The system of claim 12, where the processor reports the ratio as an indication of the age of the olive oil.

14. A method for selectively filtering 1,2-diolein and 1,3-dioleine ions from an olive oil sample, comprising:
   instructing an ion source to ionize a mixture of an olive oil sample and a pre-ionization modifier using a processor;
   instructing a differential mobility spectrometry (DMS) device to separate ions received from the ion source and affected by a post-ionization modifier based on ion mobility using the processor;
   instructing the DMS device to selectively filter separated 1,2-diolein precursor ions by selecting a first compensation voltage (CoV) for the DMS device using the processor; and
   instructing the DMS device to selectively filter separated 1,3-diolein precursor ions by selecting a second CoV for the DMS device using the processor.

15. A computer program product, comprising a non-transitory and tangible computer-readable storage medium whose contents include a program with instructions being executed on a processor so as to perform a method for selectively filtering 1,2-diolein and 1,3-dioleine ions from an olive oil sample, the method comprising:

providing a system, wherein the system comprises one or more distinct software modules, and wherein the distinct software modules comprise a control module;
instructing an ion source to ionize a mixture of an olive oil sample and a pre-ionization modifier using the control module;
instructing a differential mobility spectrometry (DMS) device to separate ions received from the ion source and affected by a post-ionization modifier based on ion mobility using the control module;
instructing the DMS device to selectively filter separated 1,2-diolein precursor ions by selecting a first compensation voltage (CoV) for the DMS device using the control module; and
instructing the DMS device to selectively filter separated 1,3-diolein precursor ions by selecting a second CoV for the DMS device using the control module.

* * * * *